United States Patent [19]

Steer

[11] Patent Number: 4,909,478
[45] Date of Patent: Mar. 20, 1990

[54] TAP FOR DRAINAGE BAG

[75] Inventor: Peter L. Steer, East Grinstead, England

[73] Assignee: E. R. Squibb and Sons, Inc., Princeton, N.J.

[21] Appl. No.: 165,652

[22] Filed: Mar. 8, 1988

[30] Foreign Application Priority Data

Mar. 9, 1987 [GB] United Kingdom ............... 8705476

[51] Int. Cl.⁴ ............................................. F16K 31/00
[52] U.S. Cl. ................................. 251/352; 251/904; 604/323
[58] Field of Search .................. 251/310, 904, 352; 604/323

[56] References Cited

U.S. PATENT DOCUMENTS

| | | | |
|---|---|---|---|
| 3,276,472 | 10/1966 | Jinkens et al. | 251/904 |
| 3,598,150 | 8/1971 | Nolan | 137/625.32 |
| 3,788,599 | 1/1974 | Cloyd | 251/904 |
| 3,823,716 | 7/1974 | Hale | 128/275 |
| 4,003,403 | 1/1977 | Wehring | 251/904 |
| 4,280,498 | 7/1981 | Jensen | 128/283 |
| 4,300,560 | 11/1981 | Steer et al. | 128/283 |
| 4,449,692 | 5/1984 | Rhodes | 251/904 |
| 4,462,510 | 7/1984 | Steer et al. | 222/44 |
| 4,603,837 | 8/1986 | Steer | 251/352 |
| 4,611,785 | 9/1986 | Steer | 251/4 |
| 4,634,437 | 1/1987 | Lowthian | 604/323 |
| 4,640,494 | 2/1987 | Steer | 251/354 |

FOREIGN PATENT DOCUMENTS

| | | |
|---|---|---|
| 1016018 | 1/1966 | United Kingdom . |
| 1198382 | 7/1970 | United Kingdom . |
| 1308519 | 2/1973 | United Kingdom . |
| 1310581 | 3/1973 | United Kingdom . |

Primary Examiner—A. Michael Chambers
Attorney, Agent, or Firm—Donald J. Barrack; Robert E. Lee, Jr.

[57] ABSTRACT

A drainage tap can be readily fixed in a face-to-face manner to the wall of a plastics drainage bag and is easily operated by a user. The tap has a body and a valve member therein, and the latter is held within the body by engagement of an external rib on the valve member in a slot which extends into a flange of the body.

6 Claims, 3 Drawing Sheets

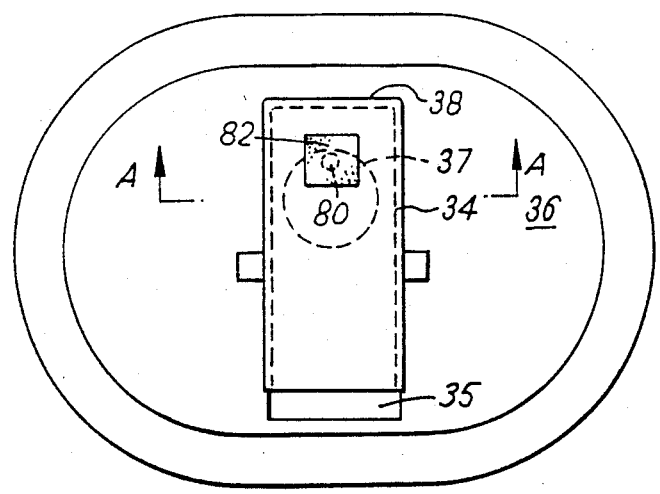
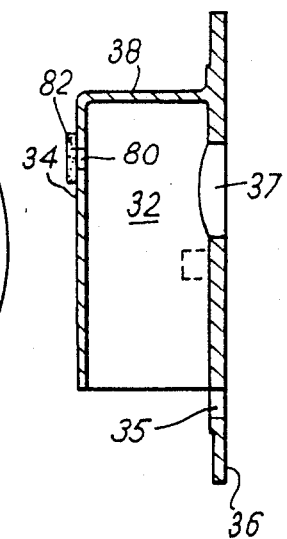
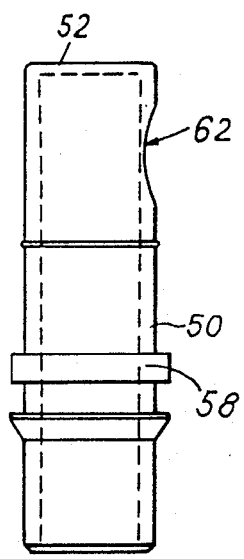
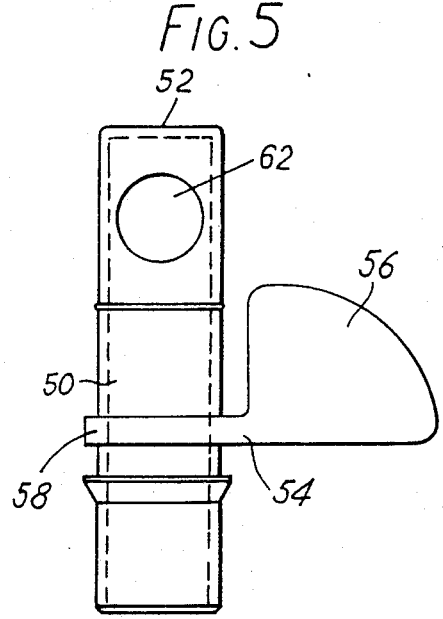

TAP FOR DRAINAGE BAG

BACKGROUND OF THE INVENTION

This invention relates to a tap for a drainage bag.

Taps for drainage bags are known. One known design of tap is known as the CARMO tap and has a tubular valve member within a tubular housing. The valve member is moved axially of the housing to expose and close off the taps by alignment and non-alignment of respective ports in the housing and the valve member. This tap is inexpensive but is not easy to fit to a bag by a rapid mass-production process and is difficult for a user (particularly an aged or infirm user) to manipulate. Similar designs of tap are shown in British Patent Specification Nos. 1 016 018 and 1 198 382.

Other known forms of tap are shown in British Patent Specification Nos. 1 308 519 and 1 310 581.

SUMMARY OF THE INVENTION

The present invention aims to provide a tap which can be readily fixed in a face-to-face manner to a wall of a plastics drainage bag and which is easily operated by a user.

According to the invention, a tap for a drainage bag has a body and a valve member therein, and the latter is held within the body by engagement of an external rib portion on the valve member in a slot extending into a flange of the body.

According to an advantageous embodiment of the invention, there is provided a tap for a drainage bag which includes two interengageable parts, namely a first part in the form of a body having a substantially cylindrical recess and a flange whereby it may be secured to the wall of the bag and a second part in the form of a valve member insertable and rotatable in the recess, in which the valve member is in the form of a substantially hollow tube having a port which at one rotational position of the member relative to the body registers with a port in the body, the valve member having an external rib extending substantially radially outwardly from the tube, and in which the flange is provided with a slot which receives the rib to prevent the valve member separating from the body in normal use.

According to a preferred feature of the invention, the handle is in the form of a flat blade secured to or integral with an arm projecting radially outwardly from the valve member. The handle may have one side marked or coded (e.g. by colour) to indicate "closed" and the other side to indicate "open". The body is preferably of plastics material and integral with the flat flange. Such a flange is readily heat-welded or adhesively fixed in a face-to-face manner to a wall of the bag, and such fixing is particularly well suited to rapid mass-production methods of manufacture.

The body and the valve member can be separated when it is desired to clean or sterilize the tap.

BRIEF DESCRIPTION OF THE DRAWINGS

The invention will be better understood from the following non-limiting description of an embodiment of the invention, given with reference to the accompanying illustrated drawings, in which:

FIG. 2 is a front view of the body part of a tap as shown in FIG. 1;

FIG. 3 is a side view of the body shown in FIG. 2;

FIG. 4 is a side view of a valve member part of a tap as shown in FIG. 1;

FIG. 5 is a part view of a valve member shown in FIG. 4;

DETAILED DESCRIPTION OF THE INVENTION

Figure 1:
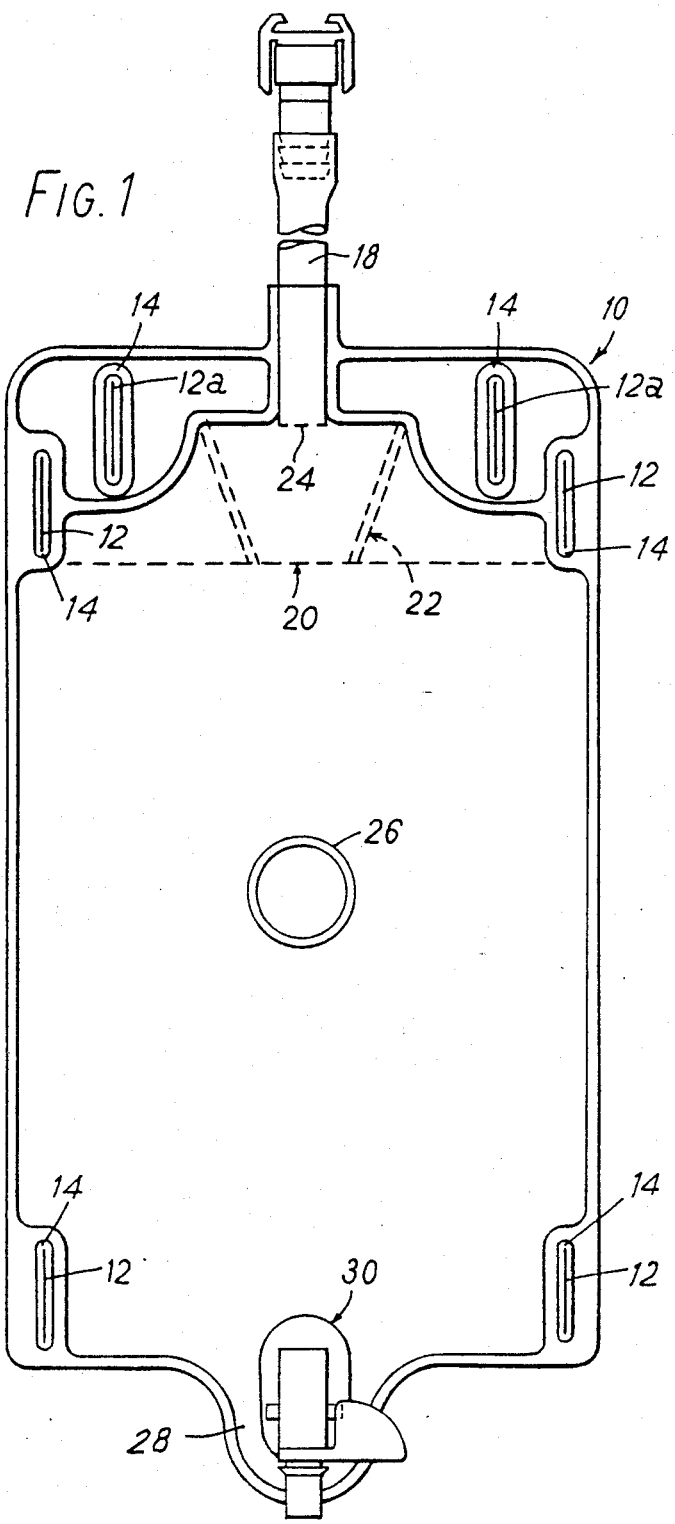
FIG. 1 is a front view of a drainage bag including an example of tap according to the invention.
Figure 6:
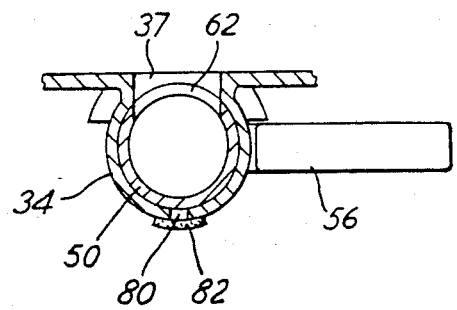
FIG. 6 is a horizontal cross-section on the line A—A through a tap in accordance with the invention illustrating the "open" position.

The drainage bag illustrated in FIG. 1 is made from two sheets of plastics material which are welded together around their edges by a weld seam of the "double tramline" type. This seam is shown at 10. A number of slits 12 are provided through the superposed pair of plastics sheets which constitute the walls of the bag, these slits being surrounded by strengthening beads generally indicated at 14. These slits are provided to receive straps or tapes for fastening the bag to a leg, and there are also slits 12a to facilitate hanging the bag up if desired. The bag is integral with an inlet tube 18. The upper region of the bag includes a non-return or anti-reflex valve generally indicated at 20. This is made of a single patch of plastics material which in combination with one of the walls of the bag, to which it is welded as shown at 22, defines a liquid entry space immediately downstream of the outlet 24 of the tube 18.

The bag walls are welded together by a closed-loop weld 26 which is of circular configuration. This is to prevent undue "pouching" or "bulging" of the bag as it fills with liquid.

While the bag is generally rectangular, its lower region has a downwardly extending extension to receive the tap which is welded or otherwise secured thereto. The extension is shown at 28 and the tap at 30.

The tap is a two part tap and its body is shown in FIGS. 2 and 3 and its valve member in FIGS. 4 and 5. The valve body shown in FIGS. 2 and 3 is of plastics material and may be injection molded. It defines a generally cylindrical recess 32, and the substantially cylindrical wall 34 of this is integral with a flat flange 36. The recess is closed by a top wall 38. The flange 36 has a slot 35 whose purpose is to receive a rib on the valve member to prevent undesired separation of the valve member from the valve body. A liquid exit port 37 extends through the flange 36 and the wall 34 and opens into the recess 32. When the valve body is secured to the wall of the bag, this port is aligned with a hole or aperture pre-punched in the bag wall. In this way a liquid communication path extends from the interior of the bag to the recess 32.

The valve member shown in FIGS. 4 and 5 may also be injection molded from plastics material and includes a substantially tubular hollow housing 50 closed at one end by a wall 52 and having extending radially outwardly therefrom an arm 54. A flat plate 56 is integral with the arm 54 and extends upwardly therefrom. The plate 56 serves as a deformable handle portion of the valve member. One surface of the plate 56 may bear the legend "closed" and the other (non-visible) surface may bear the legend "open". A liquid exit port 62 is provided in the housing 50 and this port 62 registers with the port 37 when the valve member is in one rotational position relative to the valve body, and is closed off by the valve body when the valve member is in other rotational positions relative to the valve body. In normal use, the handle 56 will be moved between its two possible limit positions in one of which it is generally parallel to the flange 36 at one side of the central axis and in the other of which it is generally parallel to the flange 36 on the other side of the central axis. When the ports 37, 62 are in registry the "open" legend is exposed whereas when the handle 56 and arm 34 are positioned as shown in FIG. 5 the "closed" legend is exposed. This arrangement is particularly convenient and is easily operated even by old and infirm people; moreover, the clear legend on the handle avoids any confusion between whether the tap is closed or open.

A rib 58 extends radially outwardly from and around the valve member tubular housing 50 and merges into the handle plate 56. It serves to partly stiffen the handle. It also extends into the slot 35 in the flange 36 and so prevents relative axial movement between the valve member and the valve body except when the plastics material of the flange 36 is forcibly deformed. This deformation would be done upon initial assembly of the tap, and could be done subsequently if for any reason it was necessary to separate the valve body and the valve member. In normal use the rib 58 and the slot 35 prevent separation of these two parts.

Figure 7:
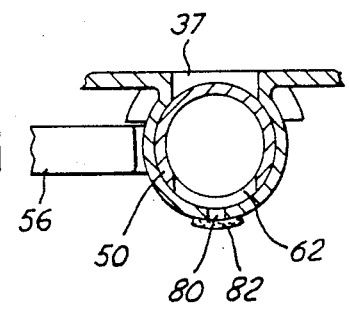
FIG. 7 is a view similar to FIG. 6 illustrating the tap in its "closed" position, wherein an air entry path to the outlet tube is provided.

Referring now to FIGS. 1, 2, 6 and 7, the valve body 34 has a hole 80 therein which as an optional feature of this embodiment of the invention is covered by a pad 82 of air-permeable material. The pad 82 may for example be of the material known by the Trade Name MICROPORE. It may carry a bacteriacide or odor-removing substance if desired. The pad 82 may be attached to the body 34 by adhesive. The hole 80 may be located so that it is aligned as seen in FIG. 7 with the hole 62 when the tap is in its closed position, and is shut off by the valve member 50 when the tap is in its open position. It will be seen that when the tap is closed air can enter to the interior of the valve member 50 and hence to the interior of a drainage tube extending downwardly from the tap outlet. In this way build-up of negative pressure in drainage tube ("pooling") can be largely prevented and usually wholly avoided. This is achieved while precluding any exit of liquid through the hole 80.

I claim:

1. A tap for a drainage bag which includes two interengageable parts, namely a first part in the form of a body having a substantially cylindrical recess and a flat flange integrally formed with said body for securing the first part to the wall of the bag and a second part in the form of a valve member insertable and rotatable in the recess, in which the valve member is in the form of a substantially hollow tube having a port which at one rotational position of the member relative to the body registers with a port in the body, the valve member having an external rib extending substantially radially outwardly from the tube, and in which the flange is provided with a slot which receives the rib to prevent the valve member separating from the body in normal use.

2. A tap according to claim 1 including a handle which is in the form of a flat blade secured to or integral with an arm projecting radially outwardly from the said valve member.

3. A tap according to claim 2 which has one side of the handle marked or coded to indicate whether the tap is open or closed.

4. A tap according to claim 1 in which the slot in the flange is a through slot.

5. A tap according to claim 1 in which the slot in the flange is a blind slot.

6. A tap according to claim 1 in which the body is integral with or secured to a flat flange of plastics material, the flange being such that it can be secured in a face-to-face manner to a wall of the bag.

* * * * *